United States Patent [19]
Griffith et al.

[11] Patent Number: 5,607,935
[45] Date of Patent: Mar. 4, 1997

[54] 2-HETEROCYCLICETHYLAMINE DERIVATIVES AND THEIR USE AS PHARMACEUTICALS

[75] Inventors: Ronald C. Griffith; Richard J. Schmiesing, both of Pittsford; Robert J. Griffith, Brighton, all of N.Y.

[73] Assignee: Fisons Corporation, Rochester, N.Y.

[21] Appl. No.: 232,029

[22] PCT Filed: Oct. 28, 1992

[86] PCT No.: PCT/GB92/01971

§ 371 Date: Aug. 1, 1994

§ 102(e) Date: Aug. 1, 1994

[87] PCT Pub. No.: WO93/09095

PCT Pub. Date: May 13, 1993

Related U.S. Application Data

[63] Continuation-in-part of Ser. No. 785,590, Oct. 30, 1991, abandoned.

[51] Int. Cl.⁶ ................ A61K 31/495; C07D 241/02
[52] U.S. Cl. ............ 514/255; 544/336; 544/406; 544/407; 544/408; 544/409
[58] Field of Search ................ 544/336, 406, 544/407, 408, 409; 514/255

[56] References Cited

U.S. PATENT DOCUMENTS

| | | | |
|---|---|---|---|
| 4,762,834 | 8/1988 | Combourieu et al. | 544/336 |
| 4,833,143 | 5/1989 | Armitage et al. | 544/336 |
| 4,968,676 | 11/1990 | Zipperer et al. | 544/336 |

FOREIGN PATENT DOCUMENTS

| | | |
|---|---|---|
| A0278090 | 8/1988 | European Pat. Off. . |
| A0346791 | 12/1989 | European Pat. Off. . |
| A0356035 | 2/1990 | European Pat. Off. . |
| A0446097 | 9/1991 | European Pat. Off. . |
| A2447258 | 4/1976 | Germany . |

OTHER PUBLICATIONS

Chemical Abstracts, #115:85433j, Griffith et al "Use of arylalkylamides in the treatment . . . " vol. 115, 1991.
I. A. Cliffe et al. "Sterically hindered lithium . . . " Synthesis, No. 12, Sep. 1985, Stuttgart De, pp. 1138–1140.
S. Fustero et al. "Synthesis and reactivity of beta–amino . . . " Tetrahedron Letters, vol. 33 No. 26, 23 Jun. 1992, Oxford GB, pp. 3801–3804.

*Primary Examiner*—Jane Fan
*Attorney, Agent, or Firm*—Nixon & Vanderhye

[57] ABSTRACT

Compounds of formula (I), wherein A represents CH=CH; Q represents pyrazine having substituents $R^6$ and $R^7$; $R^1$ represents H or $C_{1-6}$ alkyl; $R^2$ represents H, $C_{1-6}$ alkyl, $C_{3-6}$ alkenyl, $C_{3-6}$ alkynyl, $C_{3-6}$ cycloalkyl or $NH_2CH_2CO$—; $R^3$ represents H, $C_{1-6}$ alkyl, $C_{3-6}$ alkenyl or $C_{3-6}$ alkynyl; $R^4$ and $R^5$ independently represent H, OH, $C_{1-6}$ alkoxy, $C_{1-6}$ alkyl, halogen, trifluoromethyl or $NR^8R^9$; $R^6$ and $R^7$ independently represent H, OH, $C_{1-6}$ alkoxy, $C_{1-6}$ alkyl, halogen, trifluoromethyl, $C_{1-6}$ hydroxyalkyl, amidino, $CONH_2$ or $NR^8R^9$; in addition, $R^6$ and $R^7$ may independently represent O when substituted on N; $R^8$ and $R^9$ independently represent H or $C_{1-6}$ alkyl; and pharmaceutically acceptable derivatives thereof. The compounds are useful as pharmaceuticals, in particular in the treatment of neurological disorders.

7 Claims, No Drawings

2-HETEROCYCLICETHYLAMINE DERIVATIVES AND THEIR USE AS PHARMACEUTICALS

This is a continuation-in-part application of Ser. No. 785,590 filed Oct. 30, 1991 now abandoned and a 371 of PCT/GB92/01971 Oct. 28, 1992.

This invention relates to 2-heterocyclicethylamine derivatives, processes for their preparation, pharmaceutical formulations comprising them, and to their use as pharmaceuticals, in particular in the treatment of neurological disorders.

Compounds which possess anticonvulsant or N-methyl-(d)-aspartate (NMDA) blocking properties are useful in the treatment and/or prevention of neurological disorders such as stroke, cerebral ischaemia, cerebral palsy, hypoglycaemia, epilepsy, Alzheimer's disease, Huntington's chorea, Olivo-ponto-cerebellar atrophy, perinatal asphyxia, Parkinson's disease, anoxia and neuronal damage associated with substance abuse, for example, narcotics or cocaine. Undesirable side effects are associated with some neuroprotective agents and compounds with minimal psychotomimetic effects are desirable.

Certain 2-heteroarylethylamines and derivatives thereof have been described as pharmaceuticals. For example, European Patent Application No. 346791 describes 1,2-diarylethylamines in which the amine group is a cyclic amine as useful for controlling neuropathological processes and the neurodegenerative consequences thereof in mammals. U.S. Pat. No. 4,769,466 describes N-(2-aminoacetyl) -derivatives of 1,2-diarylethylamines in which one of the aryl groups is pyridine and the other is phenyl as anticonvulsants. European Patent Application No. 356035 discloses α-phenyl-2-pyridineethanamine as being useful for the treatment of neurological disorders.

Other 2-heteroarylethylamines and derivatives thereof have been described without mention of pharmaceutical utility. For example U.S. Pat. No. 4,769,466 describes 1,2-diarylethylamines in which one of the aryl groups is pyridine and the other is phenyl as intermediates. German Patents Nos. 2447258 and DE 2415063 disclose 4-methyl, 5-ethyl and 6-methyl-α-phenyl-2-pyridineethanamine, α-(2-furanyl)- and α-(2-thienyl)-2-pyridineethanamine as intermediates to the corresponding amidines. Cliffe et al, Synthesis (12), 1138–1140 (1985) describe N-(1,1-dimethylethyl)-α-phenyl-2-pyridineethanamine as an example of a highly hindered sec-alkyl-tert-alkylamine. Shuman et al, J Org Chem 27,1970–1972 (1962) describe N-[α-(2-pyridinylmethyl)benzyl] acetamide as an intermediate.

According to the invention, there is provided a compound of formula I,

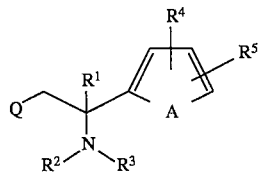

wherein

A represents CH=CH, S or O;

Q represents a 5-or 6-membered unsaturated heterocyclic ring having a nitrogen atom in the position adjacent to the point of attachment, 0-3 further heteroatoms selected from N, O and S, and substituents $R^6$ and $R^7$;

$R^1$ represents H or $C_{1-6}$ alkyl;

$R^2$ represents H, $C_{1-6}$ alkyl, $C_{3-6}$ alkenyl, $C_{3-6}$ alkynyl, $C_{3-6}$ cycloalkyl or $NH_2CH_2CO-$;

in addition, $R^1$ and $R^2$ taken together may form a $C_{3-5}$ alkylene chain;

$R^3$ represents H, $C_{1-6}$ alkyl, $C_{3-6}$ alkenyl or $C_{3-6}$ alkynyl.

$R^4$ and $R^5$ independently represent H, OH, $C_{1-6}$ alkoxy, $C_{1-6}$ alkyl, halogen, trifluoromethyl or $NR^8R^9$;

$R^6$ and $R^7$ independently represent H, OH, $C_{1-6}$ alkoxy, $C_{1-6}$ alkyl, halogen, trifluoromethyl, $C_{1-6}$ hydroxyalkyl, amidino, $CONH_2$ or $NR_R^9$;

in addition, $R^6$ and $R^7$ may independently represent O when substituted on N;

$R^8$ and $R^9$ independently represent H or $C_{1-6}$ alkyl; provided that:
(1) when A represents C=C; $R^2$, $R^3$, $R^4$ and $R^5$ each represent H; and Q represents 2-pyridinyl, 4-or 6-methyl-2-pyridinyl or 5-ethyl- 2-pyridinyl; then $R^1$ is other than H;
(2) when A represents C=C; $R^2$ represents t-butyl or $NH_2CH_2CO—$; $R^3$, $R^4$ and $R^5$ each represent H; and Q represents 2-pyridinyl; then $R^1$ is other than H;
(3) when A represents S or O; $R^2$ and $R^3$ represent H; and Q represents 2-pyridinyl; then, either $R^1$ or one of $R^4$ and $R^5$ is other than H;

and pharmaceutically acceptable derivatives thereof.

Specific heterocyclic rings which Q may represent include non-aromatic rings such as thiazoline, diazoline and oxazoline. However, Q preferably represents an aromatic ring, for example pyridine, pyrazine, pyrimidine, pyridazine, 1,2,4-triazine, imidazole, pyrazole, 2H-pyrrole, isoxazole, isothiazole, oxazole, thiazole, 1,2,4 -oxadiazine, 1,2,4-thiadiazine and 1,2,4-triazole.

Alkyl groups which $R^1$, $R^2$, $R^3$, $R^4$, $R^5$, $R^6$, $R^7$, $R^8$ and $R^9$ may represent include methyl, ethyl, propyl, isopropyl, n-butyl, iso-butyl and s-butyl. Alkoxy groups which $R^4$, $R^5$, $R^6$ and $R^7$ may represent include methoxy, ethoxy and propoxy. Halogen groups which $R^4$, $R^5$, $R^6$ and $R^7$ may represent include fluorine, chlorine, bromine or iodine. Alkenyl groups which $R^2$ and $R^3$ may represent include 2-propenyl, 2-butenyl and 2-methyl-2-propenyl. Alkynyl groups which $R^2$ and $R^3$ may represent include 2-propynyl and 2-butynyl. Cycloalkyl groups which $R^2$ and $R^3$ may represent include cyclopropyl, cyclobutyl, cyclopentyl and cyclohexyl.

Preferably, A represents CH=CH; Q represents 2-pyridinyl or 2-pyrazinyl; $R^1$ represents $C_{1-6}$ alkyl (in particular methyl); $R^2$ is hydrogen, methyl, ethyl, isopropyl or $NH_2CH_2CO—$; $R^3$ is hydrogen; $R^4$, $R^5$, $R^6$ and $R^7$ each represent H.

A preferred group of compounds which may be mentioned is that defined by formula Ia,

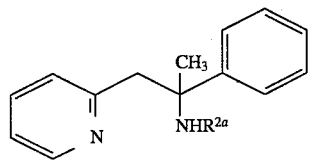

in which $R^{2a}$ represents H, methyl, ethyl or propyl.

Pharmaceutically acceptable derivatives of the compounds of formula I include pharmaceutically acceptable acid addition salts, quaternary salts and compounds which will be suitable bioprecursors (prodrugs) to the compounds of formula I. Of particular interest are acid addition salts.

Pharmaceutically acceptable acid addition salts of the compounds of formula I include salts of mineral acids, for example, hydrohalic acids (such as hydrochloric or hydrobromic); or organic acids, for example, formic, acetic or lactic acids.

Quaternary salts of the compounds of formula I include salts of $C_{1-6}$ alkyl halides.

Bioprecursors of the compounds of formula I include urethane derivatives and amino acid amide derivatives of one or more of the amino groups, and when a compound of formula I bears a hydroxyl group, esters of alkanoic and amino acids. Urethane derivatives include $C_{1-6}$ alkoxycarbonyl groups. Amino acid amide and ester derivatives may be formed from α-amino acids.

Certain compounds of formula I are optically active. All optical isomers are included within the scope of the invention.

According to a second aspect of the invention, there is provided a process for the preparation of a compound of formula I, or a pharmaceutically acceptable derivative thereof, which comprises:

(a) preparing a compound of formula I in which $R^1$, $R^2$ and $R^3$ each represent hydrogen, by reacting a corresponding compound of formula II,

Q—CH₃      II wherein Q is as defined in claim 1, with a compound of formula III,

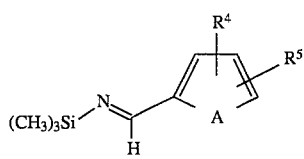

wherein $R^4$, $R^5$ and A are as defined in claim 1, in the presence of a base;

(b) preparing a compound of formula I in which $R^2$ and $R^3$ represent hydrogen, by reacting the corresponding azide of formula IV,

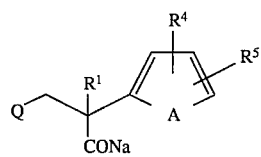

in which Q, $R^1$, $R^4$, $R^5$ and A are as defined in claim 1, under Curtius reaction conditions;

(c) preparing a compound of formula I in which $R^2$ represents H and $R^3$ represents $C_{1-6}$ alkyl, by reduction of a corresponding compound of formula IVa,

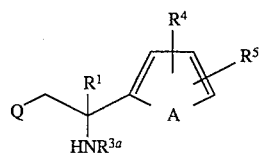

wherein $R^{3a}$ represents $C_{1-6}$ alkanoyl and Q$R^1$, $R^4$, $R^5$ and A are as defined in claim 1;

(d) preparing a compound of formula I in which one or both of $R^2$ and $R^3$ represents methyl, by reacting the corresponding compound of formula I in which one or both of $R^2$ and $R^3$ is hydrogen with formaldehyde and formic acid;

(e) preparing a compound of formula I in which $R^2$ or $R^3$ represents $C_{1-6}$ alkyl, $C_{3-6}$ alkenyl or $C_{3-6}$ alkynyl by reacting the corresponding compound of formula I in which $R^2$ or $R^3$ represents hydrogen with an alkylating agent of the formula $R^{10}$-M, in which $R^{10}$ represents a $C_{1-6}$ alkyl, $C_{3-6}$ alkenyl or $C_{3-6}$ alkynyl group and M represents a suitable leaving group;

(f) preparing a compound of formula I in which $R^1$ represents H or $C_{1-6}$ alkyl, $R^2$ represents $C_{2-6}$ alkyl or $C_{3-6}$ cycloalkyl, $R^3$ represents H and, in addition, $R^1$ and $R^2$ taken together may form a $C_{3-5}$ alkylene chain, by reduction of the corresponding imine of formula V,

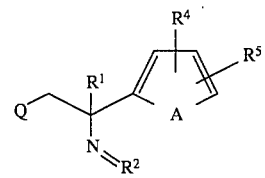

wherein Q, $R^1$, $R^4$, $R^5$ and A are as defined in claim 1, $R^2$ represents $C_{2-6}$ alkylidene or $C_{3-6}$ cycloalkylidene, and, in addition, $R^1$ and $R^2$ taken together may form a $C_{3-5}$ alkylidene chain;

(g) preparing a compound of formula I in which $R^1$, $R^2$ and $R^3$ represent hydrogen, by reductive amination of the corresponding ketone of formula VI,

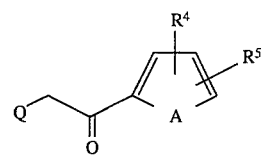

wherein Q, A, $R^4$ and $R^5$ are as defined in claim 1;

(h) preparing a compound of formula I in which $R^1$, $R^2$ and $R^3$ represent hydrogen, by reduction of a corresponding compound of formula VII,

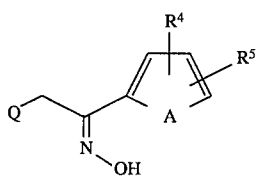

wherein Q, A, $R^4$ and $R^5$ are as defined in claim 1;

(i) preparing a compound of formula I in which $R^2$ represents —OCCH₂NH₂, by reacting a corresponding compound of formula VIIa,

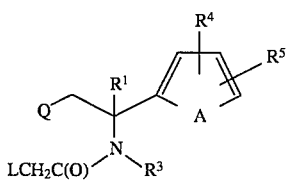

wherein L is a suitable leaving group and Q, A, $R^1$, $R^3$, $R^4$ and $R^5$ are as defined in claim 1, with ammonia; or (j) preparing a compound of formula I by removal of a protecting group from an amino- or hydroxy-protected analogue of a compound of formula I; and where desired or necessary converting the resulting compound of formula I into a pharmaceutically acceptable derivative thereof or vice versa.

In the reaction of process (a) suitable bases include, for example, butyl lithium or lithium bis(trimethylsilyl)amide, in an aprotic solvent or a mixture of solvents, for example, tetrahydrofuran or hexanes and at a temperature of, for example, from −80°–30° C.

The rearrangement of process (b) may be carried out in an inert solvent, for example, toluene, at a temperature of, for example, from 50°–150° C. Hydrolysis of the corresponding isocyanate formed in situ may be accomplished with water to give the corresponding amine or with an alcohol, for example, benzyl alcohol or ethanol, to give the corresponding carbamate.

The reduction of process (c) may be carried out with a hydride reducing agent, for example, diborane or sodium bis(2-methoxyethoxy)aluminum hydride in an aprotic solvent, for example, tetrahydrofuran. The reduction may be carried out at a temperature of, for example, from 0°–100° C.

In the reaction of process (d), methylation is accomplished by heating the amine with formic acid and formaldehyde at a temperature of, for example, from 50°–100° C. In the reaction of process (e), suitable leaving groups which M may represent include, for example, halogen, preferably chlorine, bromine or iodine, or an alkyl- or aryl-sulphonate group, for example, mesylate or tosylate. The alkylation reaction may be carried out in an aprotic solvent, for example, acetonitrile, in the presence of a base, for example, potassium carbonate, and at a temperature of, for example, from 0°–100° C.

The reduction of process (f) may be carried out with a hydride reducing agent, for example, sodium borohydride, in a protic solvent, for example, methanol, and at a temperature of, for example, from 0°–80° C.; or the reduction may be carried out in the presence of hydrogen and a hydrogenation catalyst, for example, platinum in a protic solvent such as a lower alkanol, for example, ethanol and at a temperature of, for example, from 0°–50° C.

The reaction of process (g) may be carried out in a protic solvent, for example, alkanol such as methanol, in the presence of a hydride reducing agent, for example, sodium cyanoborohydride, and an ammonium salt, for example, ammonium acetate, and at a temperature of, for example, from 0°–80° C.

The reduction of process (h) may be carried out in the presence of hydrogen and a hydrogenation catalyst, for example, platinum in a protic solvent such as a lower alkanol, for example, ethanol, or an alkanoic acid such as acetic acid, and at a temperature of, for example, from 0°–80° C.

In the reaction of process (i) suitable leaving groups which L may represent include halogen, especially chlorine or bromine. The reaction may be carried out in a protic solvent, for example, ethanol, and at a temperature of, for example, from 0°–100° C.

In the reaction of process (j), removal of the protecting group depends on the nature of the protecting group and includes acidic or basic cleavage or hydrogenolysis. Suitable amine protecting groups are, for example, benzyl, ethoxycarbonyl, benzyloxycarbonyl, t-butyloxycarbonyl or $C_{1-6}$ alkanoyl. One particularly suitable protecting group is benzyloxycarbonyl, which may readily be removed by hydrogenolysis or hydrogen bromide in acetic acid. Other groups that may be mentioned include t-butyloxycarbonyl, (Boc) which is removed by cold trifluoroacetic acid. Further protecting groups and methods for their removal are described in T W Greene, Protective Groups in Organic Synthesis, Wiley-Interscience, 1981.

It will be appreciated by those skilled in the art that in processes (a)–(i) above certain functional groups in the reactants (for example when $R^4$, $R^5$, $R^6$ or $R^7$ represent OH) are advantageously protected by a suitable protecting group (for example to avoid their transformation by the reaction conditions), which may be removed subsequently as described in process (j).

Functional groups which $R^4$, $R^5$, $R^6$ and $R^7$ may be interconverted, introduced, or derived from appropriate precursors using conventional methods. The reaction conditions of processes (a)–(i) above may also be used to interconvert, derive or introduce such functional groups.

The starting materials for the products of reaction (b), may be obtained by, for example, (1) reacting a compound of the formula VIII,

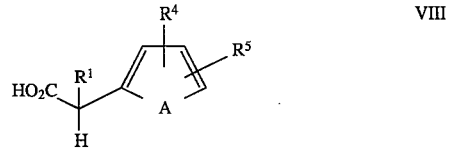

in which $R^1$, $R^4$, $R^5$ and A are as defined above with a compound of the formula IX,

in which Q is as defined above and Y represents a suitable leaving group, for example, halogen, to give the corresponding compound of formula X,

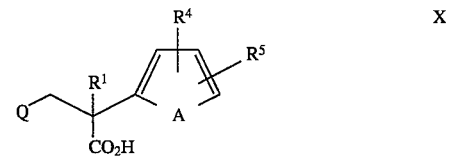

and then (2) reacting the compound of formula X with an azide. The reaction of step (1) may be carried out in the presence of a base, for example, n-butyl lithium in an inert solvent or mixtures of solvents, for example, hexanes, tetrahydrofuran or hexamethylphosphoramide. The reaction may be carried out at a temperature of, for example, from 0°–50° C. The reaction of step (2) may be carried out in a number of ways as described, for example, in J. March, Advanced Organic Chemistry, Wiley-Interscience, 1985. One method which may be mentioned is achieved by reacting the acid of formula VIII with diphenylphosphoryl azide in the presence of a base, for example, triethylamine, in an inert solvent, for example, toluene at a temperature of, for example, from 20°–120° C.

The starting material for reaction (c) may be obtained from the corresponding compound of formula I in which $R^2$ or $R^3$ represent hydrogen by conventional acylation techniques for amines. For example, $C_{26}$ alkanoyl halides or anhydrides may be reacted in the absence of a solvent; however, a suitable inert solvent may be used, for example, toluene, methylene chloride or tetrahydrofuran. The reactions may be carried out in the presence of a base, for example, a tertiary amine such as pyridine. The reactions may be carried out at a temperature of, for example, from 0°–100° C. Another method which may be mentioned is the formation of N-formyl derivatives by reaction of the corresponding amine with the reagent formed by heating formic acid and acetic anhydride at a temperature of, for example, from 0°–75° C. Suitable solvents for the formylation reaction are aprotic solvents, for example, tetrahydrofuran at a temperature of, for example, from 0°–30° C.

The starting material for reaction (f) may be prepared by reaction of the corresponding compound of formula I in which $R^2$ and $R^3$ represent hydrogen with the corresponding aldehyde or ketone in the presence of an acid catalyst, for example, p-toluenesulphonic acid, under conditions which promote the elimination of the elements of water, for example, azeotroping with toluene. In some cases the imine is formed in situ during the reduction step, in the process known as reductive alkylation, and the reaction may be carried out in the presence of hydrogen and a hydrogenation catalyst, for example, platinum in a protic solvent such as a lower alkanol, for example, ethanol and at a temperature of, for example, from 0°–50° C. In the case where the starting material of formula V is formed with $R^1$ and $R^2$ taken together representing a $C_{3-5}$ alkylidene chain it is prepared by cyclization of the corresponding aldehyde of formula XI,

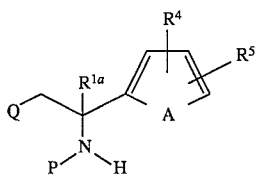

in which Q, A, $R^4$ and $R^5$ are as defined above, $R^{1a}$ represents —$(CH_2)_{2-4}$—CHO and P represents H or a protecting group removable under the cyclization conditions.

Compounds of formula XI may be prepared by hydrolysis of a corresponding compound of formula XI in which $R^{1a}$ represents a group of the formula,

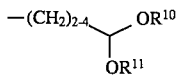

wherein $R^{10}$ and $R^{11}$ represent $C_{1-3}$ alkyl or taken together represent a $C_{2-3}$ alkylene bridge. Hydrolysis of the acetal may be carried out in aqueous media in the presence of an acid, for example, a mineral acid such as 1N Hcl, and at a temperature of, for example, from 0°–50° C. The starting materials for the acetals of formula XI may be prepared essentially according to the procedures for the preparation of the starting materials of reaction (b) described above or suitable modifications thereof as described in the examples.

The starting material for reaction (i) may be prepared from a corresponding compound of formula I in which $R^2$ is hydrogen by conventional acylation techniques, for example, by reaction with an activated carboxylic acid derivative which contains a leaving group α- to the carbonyl group, for example, chloroacetyl chloride or bromoacetyl chloride, in the presence of an acid acceptor, for example, triethylamine or pyridine.

The starting materials for reactions (a), (g) and (h) are either well known or may be prepared from known compounds by conventional methods [see for example 'Comprehensive Heterocyclic Chemistry', by Katritsky and Rees, Pergamon Press (1984)].

Pharmaceutically acceptable salts may be formed by reacting the free base, or a salt or derivative thereof with one or more equivalents of the appropriate acid. The reaction may be carried out in a solvent in which the salt is insoluble or in which the salt is soluble or in mixtures of the solvents. Acid addition salts may be converted to the corresponding base, for example, by reacting the salt with sodium hydroxide in water at room temperature. Quaternary salts may be prepared from the corresponding secondary or tertiary amines by conventional methods, for example, as described in J March, Advanced Organic Chemistry, 3rd Ed, Wiley-Interscience, 1985.

Suitable bioprecursor forms of a compound of formula I may be prepared by reacting the corresponding compound of formula I in which one or more of the amino or hydroxyl groups is unprotected with a $C_{1-6}$ alkanoic acid anhydride, $C_{1-6}$ alkanoyl halide, $C_{1-6}$ haloformate ester, or an amino acid or a carboxyl activated derivative thereof. Conventional acylation techniques for amines may be used. The reactions may be carried out in the presence of a base, for example, sodium hydroxide or pyridine. The reactions may be carried out in the absence of a solvent; however, a suitable inert solvent may be used, for example, toluene, methylene chloride or tetrahydrofuran. The reactions may be carried out at a temperature of, for example, from 0°–100° C. The condensation with α-amino acid derivatives may be carried out in conditions similar to those used for the synthesis of peptide bonds in protein chemistry, e.g. by carrying out the reaction in the presence of N,N'-carbonyldiimidazole in a polar aprotic solvent or using a hindered base, e.g. triethylamine and an alkyl chloroformate. When one or both of the amino acid nitrogen substituents is hydrogen, the nitrogen atom requires protection. One particularly suitable protecting group is benzyloxycarbonyl, which may readily be removed by hydrogenolysis or hydrogen bromide in acetic acid. Other groups that may be mentioned include t-butyloxycarbonyl (Boc), which is removed by standing the peptide in cold trifluoroacetic acid; Fmoc, which may be removed by treatment with dilute piperidine (20% in DMF); (4-methoxybenzyl)oxycarbonyl and 2-nitrophenylsulphenyl. Further protecting groups and methods for their removal are described in T W Greene, Protective Groups in Organic Synthesis, Wiley Interscience, 1981.

Suitable bioprecursor groups which may be mentioned include methoxycarbonyl, ethoxycarbonyl and α-amino acids, for example, glycine, alanine, leucine, proline, methionine, serine and sarcosine. Derivatives of α-amino acids are preferred, especially glycine.

Resolution of compounds with asymmetric centres may be accomplished by methods well known in the art, for example, by separation of their diastereoisomeric salts, chromatography on a chiral column or asymmetric syntheses. Methods of resolution are described in J. March, Advanced Organic Chemistry, 3rd. Edition, Wiley Interscience, 1985.

The compounds of formula I, and their pharmaceutically acceptable derivatives, are useful because they possess pharmacological activity in animals. In particular, the compounds have useful neuroprotective properties. Without being limited by the following explanation, the compounds are thought to possess NMDA blocking properties. Neurodegeneration is known to be caused or accelerated by certain excitatory amino acids found naturally in the central nervous system (CNS). Glutamate is an endogenous amino acid which has been characterized as a fast excitatory transmitter in the mammalian brain. Glutamate is also known as a powerful neurotoxin capable of killing CNS neurons under certain pathologic conditions which accompany stroke and cardiac arrest. It has been shown that the sensitivity of central neurons to hypoxia and ischemia can be reduced by the specific antagonism of post synaptic glutamate receptors. Glutamate is characterized as a broad spectrum agonist having activity at four neuronal excitatory amino acid receptor sites. These receptor sites are named after the amino acids which selectively excite them: kainate (KA), N-methyl-D-aspartate(NMDA), quisqualate(QUIS) and 2-amino-4-phosphonobutyrate (APB). Glutamate is believed to be a mixed agonist capable of binding to and exciting all four receptor types. Thus, agents which selectively block or indigenous the action of glutamate at these receptors can prevent neurotoxic injury associated with anoxia, hypoxia or ischemia. In particular, compounds which bind to the NMDA receptor site and selectively block the action of glutamate are useful in the prevention and treatment of neurodegenerative diseases.

In addition, the compounds of formula I, and their pharmaceutically acceptable derivatives, demonstrate anticonvulsant activity by their ability to inhibit maximal electroshock (MES) induced seizures in mice, certain compounds inhibit the onset of convulsions and death induced by administration of NMDA to mice and certain compounds demonstrate antihypoxia activity by their ability to increase the survival time of mice in an oxygen depleted environment.

Antiepileptic activity may be measured by assessing a compound's ability to prevent the hind limb tonic extension component of the seizure in groups of mice induced by maximal electroshock (MES) after oral or intraperitoneal administration, according to the procedures of the Epilepsy Branch, NINCDS as published by R J Porter et al, Cleve Clin Quarterly 1984, 51, 293, and compared with the standard agents dilantin and phenobarbital.

Certain compounds of this invention may possess useful antihypoxia activity. This activity may be conveniently measured in mice. Groups of mice are tested at various times after the intraperitoneal administration of graded doses of the test compound. The animals' survival time in a temperature-controlled hypoxic environment (96% nitrogen and 4% oxygen) is recorded. A statistical comparison is made between coincident vehicle treated animals and the experimental group. The dose-response and minimum active dose (MAD) for compounds are obtained. Other modes of administration can also be used.

NMDA activity may be measured in several ways:

a) NMDA blocking activity is measured by assessing a compound's ability to protect mice from convulsions induced by intravenous administration of 150 mg/kg of NMDA according to the procedures of Czuczwar et al., (Neurotransmitters, Seizures and Epilepsy III, edited by G. Nistico et al., Raven Press, New York 1986, pages 235–246). Groups of mice are pretreated by 30 minutes with the test compound by the oral or intraperitoneal routes and then given NMDA. Animals were observed for convulsions as defined by loss of righting reflex and appearance of tonic/clonic seizures. Animals are kept for 60 min after NMDA dosing and mortality was recorded.

b) NMDA receptor antagonist activity is measured in vitro by assaying a compounds ability to inhibit binding of the receptor antagonist 10,11-dihydro-5-methyl-5H-dibenzo[a,d]-cyclohepten-5,10-imine (MK801) to the receptor. The method is described by Foster and Wong, Br. J. Pharmacol. 91, 403–409 (1987).

c) NMDA and glycine receptor affinity may also be tested in the [$^3$H]L-glutamate and [$^3$H]glycine binding assays following the method of Monaghan & Cotman, PNAS, 83, 7532, (1986) and Watson et al, Neurosci Res Comm, 2, 169, (1988).

An important factor in judging the usefulness of compounds for the treatment of neurological disorders is an evaluation of their propensity to produce neurotoxic effects. Compounds may be evaluated in acute neurological impairment assays essentially according to the procedures of Coughenour et al, Pharmac Biochem Behav, 1977,6,351. The therapeutic index for a compound may then be calculated to provide an indication of the relative safety of a compound. Marked side effects of compounds may also be of significance in evaluating the usefulness of compounds.

Compounds may be evaluated for their ability to cause significant differences in symptomatology according to the criteria set forth by Irwin, Comprehensive Observational Assessment, Ia. A Systematic, Quantitative Procedure for Assessing the Behavioral and Physiologic State of the Mouse, Psychopharmacologia, 13, 222–257, (1968).

Certain compounds may act as neuromodulators by interfering with neurotransmitter uptake. Undesirable psychotomimetic effects may be associated with a compound's ability to inhibit dopamine uptake. Inhibition of dopamine uptake may be measured according to the method of Holtz et al, Molecular Pharmacol, 10, 746 (1974).

Thus, according to another aspect of the invention there is provided a method of treatment of a neurological disorder, which comprises administering to a patient in need of such treatment a therapeutically effective amount of a compound of formula I, as defined above but without proviso (3), or a pharmaceutically acceptable derivative thereof. There is further provided the use of a compound of formula I, as defined above but without proviso (3), or a pharmaceutically acceptable derivative thereof, as active ingredient in the manufacture of a medicament for use in the prevention or treatment of a neurological disorder.

Specific neurological disorders that may be mentioned include stroke, cerebral ischaemia, cerebral palsy, hypoglycaemia, epilepsy, Alzheimer's disease, Huntington's chorea, Olivo-ponto-cerebellar atrophy, perinatal asphyxia, Parkinson's Disease, anoxia and neuronal damage associated with substance abuse, for example, narcotics or cocaine. Stroke is of particular interest.

For the above-mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg; more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable derivatives thereof, may be used in the form of appropriate pharmaceutical formulations. Thus, according to a further aspect of the invention, there is provided a pharmaceutical formulation comprising a compound of formula I, as defined above but without proviso (3), or a pharmaceutically acceptable derivative thereof, in association with a pharmaceutically acceptable adjuvant, diluent or carrier.

Examples of such adjuvants, diluents and carriers are:

for tablets and dragees; lactose, starch, talc or stearic acid;

for capsules; tartaric acid or lactose;

for injectable solutions; water, alcohols, glycerin or vegetable oils;

for suppositories: natural or hardened oils or waxes.

Formulations in a form suitable for oral, i.e. oesophageal administration include tablets, capsules and dragees.

Sustained release compositions include those in which the active ingredient is bound to an ion exchange resin which is optionally coated with a diffusion barrier to modify the release properties of the resin.

We prefer such formulations to contain up to 50% and more preferably up to 25% by weight of a compound of formula I, or a pharmaceutically acceptable derivative thereof.

The compounds of formula I, and pharmaceutically acceptable derivatives thereof have the advantage that they are less toxic, more efficacious, are longer acting, have a broader range of activity, are more potent, produce fewer side effects, are more easily absorbed or have other more useful pharmacological properties, than prior art compounds in the therapeutic fields mentioned above.

The invention is illustrated by the following examples.

EXAMPLE 1

α-Methyl-α-phenyl-2-pyridineethanamine dihydrochloride a) α-Methyl-α-phenyl-2-pyridinepropanoic acid A 2.5M hexane solution of butyl lithium (440 ml) was added over 1 hour to an ice-cooled solution of phenylacetic acid (70 g, 0.51 mol), hexamethyl-phosphoramide (91 ml) and THF (tetrahydrofuran, 0.81). The reaction mixture was allowed to warm to room temperature over 1.5 hours, then cooled back to 0° C. A solution of methyl iodide (33 ml, 0.52 mol) in THF (100 ml) was added to the stirred reaction and after 15 minutes at 0° C., then 1.5 hours at room temperature the reaction was cooled back to 0° C. and butyl lithium (220 ml of a 2.5M hexane solution) was added dropwise. The reaction was stirred at 0° C. for 10 minutes and room temperature for 0.5 hour. After cooling to 0° C., a solution of picolyl chloride (0.61 mol) in THF (100 ml) was added over 0.5 hour. The ice bath was removed and the reaction was stirred overnight at room temperature. The reaction mixture was partitioned between water and ethyl acetate. The basic aqueous layer was neutralized at 0° C. with 3N HCl and the precipitated solids were filtered, washed with ether and dried to give the subtitle acid (52 g). Extraction of the aqueous filtrate with ethyl acetate and concentration of the ethyl acetate layer afforded a crude residue. The residue was triturated with ether to give an additional 25 g of product.

b) N-Carbobenzoxy-α-methyl-α-phenyl-2-pyridineethanamine

The acid (57 g) from step (a) was dissolved in toluene (1.51) and triethylamine (36.5 ml), then diphenylphosphoryl azide (54.4 ml) was added. The mixture was heated to reflux. Reflux was maintained for 3 hours; then the reaction mixture was cooled to 90° C. and benzyl alcohol (88.5 ml) was added dropwise. Refluxing was resumed and maintained overnight. Concentration of the reaction mixture afforded a dark oil. The oil was subjected to vacuum distillation to remove excess benzyl alcohol and give essentially pure subtitle compound as an oil.

c) α-Methyl-α-phenyl-2-pyridineethanamine dihydrochloride

A sample of the N-carbobenzoxy compound (4.8 g) prepared in step (b) was hydrogenated in acetic acid (75 ml) over 10% palladium-charcoal (900 mg) at 3.4 atm (50 psi) in a Parr apparatus overnight. The catalyst was filtered and the filtrate was concentrated to dryness in vacuo. The residue was chromatographed on silica gel and eluted with ammoniated 5–10% $CH_3OH/CHCl_3$ [1:19–1:9]. The amine fractions were combined to give an oil (2.1 g). The amine was converted to the hydrochloride salt by treatment with hydrogen chloride in isopropanol (30 ml) followed by addition of ethyl acetate (5 ml). The precipitated salt (2.9 g) was filtered and dried at 75° C. to give the title compound, mp 192°–196° C.

Alternative preparation of α-methyl-α-phenyl-2-pyridinepropionic acid

A 2.5M hexane solution of butyl lithium (264 ml) was added during 1 hour to an ice-cooled solution of α-methylphenylacetic acid (50 g, 0.33 mol), hexamethyl-phosphoramide (60 ml) and THF (0.41). The reaction mixture was stirred to room temperature for 0.5 hour, then cooled back to 0° C. After cooling to 0° C., a solution of picolyl chloride (0.46 mol) in THF (100 ml) was added over 0.75 hour. The ice bath was removed and the reaction was stirred overnight at room temperature. The reaction mixture was partitioned between water (500 ml) and ethyl acetate (500 ml). The organic layers were back extracted with 20% NaOH solution (200 ml). The basic aqueous layers were combined and neutralized at 0° C. with 3N HCl and the precipitated solids were filtered, washed with ether and dried to give the title acid (63 g).

EXAMPLE 2

2-Amino-N-[1-methyl-1-phenyl-2-(2-pyridinyl)ethyl] acetamide dihydrochloride a) N-(2-chloroacetyl)-α-methyl-α-phenyl-2-pyridineethanamine A solution of chloroacetyl chloride (1.7 g, 15 mmol) in $CHCl_3$ (10 ml) was added to an ice-cooled solution of the title compound of Example 1 (3 g, 14.2 mmol) and triethylamine (4.2 ml) in $CHCl_3$ (70 ml). After 2 hours, the reaction mixture was made basic with 15% NaOH solution. The organic layer was separated, dried ($MgSO_4$) and concentrated to give a residue which was chromatographed on silica gel and eluted with ethyl acetate/hexane [1:1] to give 2.7 g of the subtitle compound.

b) 2-Amino-N-[1-methyl-1-phenyl-2-(2-pyridinyl)ethyl] acetamide dihydrochloride

The product of step (a) was combined with similarly prepared material to give a total of 4.8 g which was dissolved in ethanol (125 ml) and charged to a Parr bomb and cooled to 0° C. Liquid ammonia (excess) was added and the sealed bomb was heated to 80° C. for 24 hours. After cooling the bomb was unsealed and the solution was concentrated to give a residue of 4.5 g. The residue was chromatographed on silica gel and eluted with ammoniated $CH_3OH/CHCl_3$ [1:9]. The fractions containing purified product were combined and concentrated to give the desired base (3.2 g). The base was converted to the hydrochloride salt by treatment with hydrogen chloride in ethanol/isopropanol solution. The solvents were evaporated and the residue was redissolved in methanol (10 ml). Ether was added to the methanol solution and the precipitated solids were isolated to give the title compound (3.6 g), mp 254°–256° C.

EXAMPLE 3

Resolution of α-methyl-α-phenyl-2-pyridineethanamine

A solution of the title compound of Example 1 (34.7 g, 0.164 mol) in 95% ethanol (170 ml) was warmed to 60° C. (−)-Dibenzoyl-L-tartaric acid monohydrate (67.8 g, 0.18 mol) was dissolved in 95% ethanol (170 ml) at 60° C. and added to the amine. The combined solutions were heated to reflux and then cooled to room temperature with stirring. After 3 days the precipitated solids were filtered to give a white solid (28.6 g). The solid was recrystallized from 95% ethanol (220 ml) to give the dibenzoyl-L-tartaric acid salt (19.5 g). A sample of the salt was converted to the hydrochloride salt via the base by conventional methods, $[\alpha]_D=$ +63.93°(c=0.964, $CH_3OH$).

The ethanolic filtrates from the two crystallization steps were concentrated and the residual salts were treated with water (200 ml) and concentrated $NH_4OH$ (100 ml). The mixture was extracted with methylene chloride and the methylene chloride layer was dried ($MgSO_4$) and concentrated to give the base (20.5 g). The base (20.5 g) was treated with (+)-dibenzoyl-D-tartaric acid (40 g) in 95% ethanol (300 ml) at 60° C. After cooling to room temperature ether (600 ml) was added. A solid precipitated and was filtered to give 41.5 g of salt. The salt was recrystallized from 95% ethanol to give 27.5 g of the enantiomeric salt. A sample of the salt was converted to the dihydrochloride salt, $[\alpha]_D=+$ 58.76° (c=1.045, $CH_3OH$).

EXAMPLE 4

α-(3-Methyl-2-thienyl)-2-pyridineethanamine dimaleate a) N-(Trimethylsilyl)-3-methyl-2-thiophene carboxaldimine The subtitle compound was prepared by adding a 1M solution of lithium bis(trimethylsilylamide) (105 ml) dropwise to an ice-cooled solution of 3-methyl-2-thiophene carboxaldehyde (11.7 g, 0.93 mol) in THF (100 ml).

b) α-(3-Methyl-2-thienyl)-2-pyridineethanamine dimaleate

A solution of 2-picoline (9 ml) in THF (100 ml) was cooled to −78° C. and 1.6M butyl lithium in hexane solution (58 ml) was added. The solution was stirred to room temperature for 30 minutes, recooled to −78° C. and then the solution of the product of step (a) was added dropwise. The reaction mixture was stirred overnight at room temperature. Ether (100 ml) was added dropwise followed by 1N HCl (100 ml). The aqueous layer was separated, basified with 50% NaOH solution and extracted with ethyl acetate. The ethyl acetate layer was separated, dried ($MgSO_4$) and concentrated to give an oil (13.5 g). The oil was purified by chromatography on silica gel and eluted with ammoniated $CH_3OH/CHCl_3$[1:9]. The purified fractions were combined to give an oil. The oil (4.1 g) was dissolved in ethanol (40 ml) and maleic acid (4.5 g) was added. After cooling to 0° C., a solid precipitated which was filtered and dried to give the title compound (5.7 g), mp 131°–134° C.

EXAMPLE 5

2-Amino-N-[1-(3-methyl-2-thienyl)-2-(2-pyridinyl)ethyl]acetamide difumarate

By following essentially the same procedure as described in Example 2 above, but substituting α-(3-methyl-2-thienyl)-2-pyridineethanamine (as prepared in Example 4) for α-methyl-α-phenyl-2-pyridineethanamine, the corresponding free base of the title compound was obtained as an oil.

The base (1.4 g) was then treated with excess fumaric acid in ethanol (40 ml). Ether (75 ml) and hexane (10 ml) were added and a white solid (1.7 g) was isolated. The solid was recrystallized from ethanol/ether to give the title compound (1.4 g), mp 174°–177° C.

EXAMPLE 6

N-Ethyl-α-(3-methyl-2-thienyl)-2-pyridineethanamine fumarate a) N-Acetyl-α-(3-methyl-2-thienyl)-2-pyridineethanamine Acetic anhydride (2.1 ml) was added to a solution of α-(3-methyl-2-thienyl)-2-pyridineethanamine (from Example 4, 3.1 g) in pyridine (20 ml). After 3 days the mixture was diluted with water and extracted with ethyl acetate. The ethyl acetate layer was dried ($MgSO_4$) and concentrated to give the subtitle acetyl derivative.

b) N-Ethyl-α-(3-methyl-2-thienyl)-2-pyridineethanamine fumarate

The product of step (a) (3.1 g) was dissolved in THF (30 ml) and cooled to 0° C. Borane-THF (1M, 59.4 ml) was added and the reaction mixture was stirred overnight. The reaction mixture was decomposed with 20 ml of 4N HCl at 0° C. The acidic mixture was basified with 50% NaOH solution at 0° C. and the resulting mixture was extracted with ethyl acetate. Concentration of the ethyl acetate layer afforded a residue which was purified by chromatography on silica gel and elution with ethyl acetate/hexane [1:1] followed by ammoniated $CH_3OH/CHCl_3$[1:19]. The purified fractions were combined to give the free base of the title compound as an oil (2 g). The base was converted to the fumarate salt with fumaric acid (2 g) in ethanol (50 ml). Ether (100 ml) and hexane (5 ml) were added and the fumarate salt of the title compound was isolated, mp 153°–154° C.

EXAMPLE 7

N-Allyl-α-phenyl-2-pyridineethanamine dihydrochloride

α-Phenyl-2-pyridineethanamine (1.5 g), potassium carbonate (1.15 g) and allyl bromide (0.74 g) were added to acetonitrile (25 ml) and the reaction mixture was heated at reflux for 3 hours. The cooled reaction mixture was poured into a mixture of water and ethyl acetate. The ethyl acetate layer was separated, dried ($MgSO_4$) and concentrated. The residue was chromatographed on silica gel and eluted with $CH_3OH/CHCl_3$[1:9]. The product-containing fractions were combined and concentrated and the amine obtained was converted to the hydrochloride by treatment with hydrogen chloride in ethyl acetate. The precipitated solids were recrystallized from methanol/ether to give the title compound (0.06 g), mp 159°–161° C.

EXAMPLE 8

2-Phenyl-2-(2-pyridinylmethyl)piperidine dihydrochloride a) α-phenyl-α-[3-(1,3-dioxolan-2-yl)propyl]-2-pyridinepropionic acid A 2.5M hexane solution of butyl lithium (180 ml) was added to an ice-cooled solution of phenylacetic acid (20 g), hexamethylphosphoramide (25.6 ml) and tetrahydrofuran (260 ml). The reaction mixture was stirred to room temperature, then cooled back to 0° C. A solution of 2-(3-chloropropyl)-1,3-dioxolane in THF (20 ml) was added dropwise and the mixture was stirred to room temperature overnight. The reaction was cooled back down to 0° C. then butyl lithium (60 ml of a 2.5M hexane solution) was added dropwise followed by picolyl chloride (0.147 mol) in THF (40 ml). The ice-bath was removed and the reaction was stirred at room temperature for 3 days. The reaction mixture was quenched with half-saturated aqueous NH$_4$Cl. Ethyl acetate and chloroform were added to dissolve the solids. The aqueous layer was neutralized with 1N HCl and extracted with chloroform. The combined organic layers were dried (MgSO$_4$) and concentrated to give a solid which was washed with ether to give the subtitle compound (28.1 g).

b) N-carbobenzoxy-α-[3-(1,3-dioxolan-2-yl)propyl]-α-phenyl-2-pyridineethanamine

The acid of step (a) (25 g), triethylamine (11.2 ml) and diphenylphosphoryl azide were dissolved in dry toluene (400 ml) and heated at reflux for 3 hours. Benzyl alcohol (30.4 ml) was added dropwise and the resulting mixture was refluxed overnight. Concentration of the reaction mixture afforded a dark oil which was purified by chromatography on silica gel and elution with ethyl acetate/hexanes [1:9–1:1] to give the subtitle compound (25 g).

c) N-carbobenzoxy-α-phenyl-α-(4-oxobutyl)-2-pyridineethanamine

The amine of step (b) (25 g) was dissolved in 1N HCl (300 ml) and stirred at room temperature overnight to hydrolyze the acetal group. The solution was neutralized with NaHCO$_3$ and the amine was extracted into chloroform. Concentration of the chloroform afforded the subtitle compound (27 g) as a yellow solid.

d) 2-Phenyl-2-(2-pyridinylmethyl)piperidine dihydrochloride

The aldehyde-amine of step (c) (27 g) was dissolved in glacial acetic acid (500 ml) and 10% Pd-C catalyst (6.0 g) was added. The reaction mixture was hydrogenated in a Parr apparatus at 2.7–3.4 atm (40–50 psi) overnight. The catalyst was filtered and the filtrate was concentrated to dryness. The residue was purified by chromatography on silica gel and elution with CH$_3$OH:CHCl$_3$[1:19]. Purified amine product (5.2 g) was obtained and converted to the dihydrochloride salt by reaction with hydrogen chloride in isopropanol/ether. The salt was recrystallized from isopropanol/ether to give a solid (1.2 g) which was then freeze-dried from an aqueous solution to give the title compound as a hydrate containing 6.4% H$_2$O, mp 193°–196° C.

EXAMPLE 9

α-Phenyl-2-pyridineethanamine 1-oxide a) 2-(2-Oxo-2-phenylethyl)-pyridine N-oxide A solution of 2-picoline N-oxide (4.4 g, 0.04 mol) in benzene (25 ml) was added to a suspension of sodium hydride (3.2 g of 60% oil dispersion) and methyl benzoate (9.94 ml, 0.08 mol) in dry benzene (100 ml). The reaction mixture was refluxed overnight. Methanol (15 ml) was added to the cooled reaction mixture, followed by water (150 ml). The aqueous layer was separated and extracted with chloroform (2×40 ml). The aqueous layer was acidified with 1N HCl and extracted with chloroform. The combined organic layers were dried (MgSO$_4$) and concentrated to give the subtitle ketone as a solid (7 g), mp 146°–148° C.

b) α-Phenyl-2-pyridineethanamine 1-oxide

The ketone (10.72 g, 0.05 mol) prepared in step (a) above was combined with ammonium acetate (38.73 g, 0.5 mol), sodium cyanoborohydride (2.22 g, 0.035 mol) and absolute methanol (200 ml) and stirred at room temperature for 3 days. The mixture was acidified to pH 1 with concentrated HCl, then the methanol was evaporated. The residue was partitioned between water and chloroform and the aqueous layer was separated and basified with solid KOH. The precipitate was extracted into chloroform and the chloroform layer was dried (MgSO$_4$). Concentration of the solvent afforded the amine as a syrup (3.3 g). The amine was converted to the hydrochloride by dissolving in ethyl acetate and adding a saturated solution of hydrogen chloride in isopropanol until acidic. The precipitated solid was filtered and recrystallized from ethanol/ether to give the title compound as a white solid (2.54 g), mp 202°–207° C. (dec).

EXAMPLE 10

α-(4-Hydroxyphenyl)-2-pyridineethanamine dihydrochloride a) α-[(4-benzyloxy)phenyl]-2-pyridineethanamine 4-(Benzyloxy)benzaldehyde (5 g, 0.023 mol) and lithium bis (trimethylsilyl)amide (27 ml of a 1M solution in THF, 0.027 mol) were mixed and stirred at 0° C. for 15 minutes, then for 1 hour at room temperature to form an imine in solution.

2-Picoline (2.3 ml, 0.023 mol) was dissolved in THF (40 ml) and cooled to –78° C. n-Butyl lithium (9.2 ml of a 2.5M hexane solution) was added and the mixture was stirred to room temperature for 30 minutes then cooled back to –78° C. The imine solution prepared above was added dropwise and the resulting mixture was stirred to room temperature overnight. Ether was added, then 1N HCl was added until the mixture was acidic, then the reaction was stirred for 30 minutes. The layers were separated and the aqueous layer was cooled to 0° C. Ethyl acetate was added and the mixture was made basic with 50% NaOH solution. The aqueous layer was extracted with ethyl acetate and the separated organic layer was dried (MgSO$_4$) and concentrated to give a syrup. The syrup was purified by chromatography on silica gel and elution with CH$_3$OH/CHCl$_3$ [1:99–1:19] to give the subtitle compound as a pale yellow syrup (4.5 g).

b) α-(4-Hydroxyphenyl)-2-pyridineethanamine dihydrochloride

The amine of step (a) (2.30 g) was dissolved in 95% ethanol (80 ml) and hydrogenated over 10% Pd-C (0.50 g) at 3.4 atm (50 psi) in a Parr apparatus overnight. The reaction mixture was mixed with additional 10% Pd-C (0.50 g) and hydrogenated for a further 5 hours. The catalyst was filtered and the filtrate was made acidic with saturated hydrogen chloride/ethanol solution. Concentration of the solvent and addition of ether afforded a precipitate on cooling the solution to 0° C. overnight. The precipitated solid was isolated and recrystallized from 95% ethanol/ether to give the title compound as the dihydrochloride salt (1.8 g), mp 297°–305° C. (dec).

EXAMPLE 11

α-Phenyl-1-methyl-2-imidazoleethanamine dihydrochloride

A 2.5 M solution of n-butyl lithium in hexane (22 ml, 0.055 mol) was added dropwise to a solution of 1,2-dimethylimidazole (4.80 g, 0.05 mol) in THF (200 ml) at 0° C.

The solution was stirred for 2 hours before it was added to a solution of N-(trimethylsilyl)benzaldimine, prepared by adding 52 ml of a 1.0M solution of lithium bis(trimethylsilyl)amide to a solution of benzaldehyde (5.31 g, 0.05 mol) in THF (25 ml) at 0° C. and stirring for 30 minutes. The reaction mixture was stirred overnight at room temperature. Water was added and the organic layer was separated. The organic layer was washed with 400 ml 1N HCl and the acid layer was basified to pH 10 and then extracted with ether (400 ml), followed by methylene chloride (200 ml). The organic extracts were combined, dried ($MgSO_4$) and concentrated to give an oil (7.0 g) which was purified by chromatography on silica gel and elution with ammoniated $CH_3OH/CHCl_3$ [1:19] to give the amine (6.5 g). The amine was converted to the dihydrochloride salt with hydrogen chloride in isopropanol. Ether was added to precipitate the solid salt which was recrystallized from 95% ethanol (60 ml) and ether (150 ml) to give the title compound as a solid (7.04 g), mp 247°–9° C. (dec).

EXAMPLE 12

N-Ethyl-α-methyl-α-phenyl-2-pyridineethanamine dihydrochloride

By following essentially the same procedures as described in Example 6 above and substituting α-methyl-α-phenyl-2-pyridineethanamine (as prepared in Example 1) for α-(3-methyl-2-thienyl)-2-pyridineethanamine the title compound was obtained, mp 200°–203° C.

EXAMPLE 13

N-Isopropyl-α-methyl-α-phenyl-2-pyridineethanamine dimaleate

By following essentially the same procedures as described in Example 7 above and substituting α-methyl-α-phenyl-2-pyridineethanamine (as prepared in Example 1) and 2-iodopropane for α-phenyl-2-pyridineethanamine and allyl bromide respectively the free base of the title compound was obtained. The base was converted to the dimaleate salt by treatment with maleic acid (2.1 equivalents) in ethyl acetate/ether and recrystallization from ethyl acetate afforded the title compound, mp 109°–111° C.

EXAMPLE 14

N,α-Dimethyl-α-phenyl-2-pyridineethanamine dihydrochloride a) N-Formyl-α-methyl-α-phenyl-2-pyridineethanamine Formic acid (98%, 1.78 ml) was added dropwise to acetic anhydride (3.47 ml) at 0° C. The resulting mixture was heated at 55° C. for 2 hours then recooled to 0° C. and diluted with THF (5 ml). A solution of α-methyl-α-phenyl-2-pyridineethanamine (as prepared in Example 1,3 g) in THF (10 ml) was added dropwise and the reaction was stirred at 0° C. for 30 minutes. The volatiles were removed by vacuum distillation to give the subtitle compound as a syrup (5 g).

b) N,α-Dimethyl-α-phenyl-2-pyridineethanamine dihydrochloride The syrup from step (a) above was dissolved in THF (40 ml) and added to 70 ml of a 1M $BH_3$:THF complex at 0° C. and the reaction mixture was stirred to room temperature overnight. Hydrochloric acid (45 ml, 5M) was added to the ice-cooled reaction mixture and stirring was continued at room temperature overnight. The reaction mixture was basified at 0° C. with 15% NaOH solution then extracted with ethyl acetate. The organic layer was separated, dried ($MgSO_4$) and concentrated to give the methyl amine as a syrup (1.7 g). The amine was purified further by chromatography on silica gel and elution with $CH_3OH/CHCl_3$[0:1–1:9]to give the base (900 mg). The base was converted to the hydrochloride salt by treatment with hydrogen chloride in isopropanol. Ether was added to precipitate the title compound (800 mg), mp 190°–194° C.

EXAMPLE 15

α-Phenyl-2-(2-pyrazine)ethanamine maleate a) N-(Trimethylsilyl)carboxaldimine

To an ice-cooled solution of benzaldehyde (4.2 g, 0.039 mol) in THF (150 ml) was added dropwise 40 ml of a 1M solution of lithium bis(trimethylsilyl)amide in THF. The resulting mixture was stirred at 0° C. for 15 minutes, then for 1 hour at room temperature to form the subtitle compound in solution.

b) α-Phenyl-2-(2-pyrazine)ethanamine maleate

To the imine solution obtained above at 0° C. was added in one portion 2-methylpyrazine (3.7 g, 0.039 mol) followed by dropwise addition of a 1M solution of lithium bis(trimethylsilyl)amide in THF until the mixture darkened (approximately 3 ml). The reaction mixture was stirred overnight at room temperature, cooled to 0° C., diluted with 100 ml of ether, and treated with dropwise addition of 1N HCl until pH 1–2 was maintained. The aqueous layer was separated, made basic with 20% NaOH solution, and extracted with chloroform (3×). The chloroform extracts were washed with water, brine, dried and concentrated to give an oil (6.1 g). The oil was purified by chromatography on silica gel eluting with ammoniated $CH_3OH/CHCl_3$ [1:19], taken up in ethanol and treated with maleic acid (1.1 equivalents). The resulting white solid was collected by filtration and dried to give the title compound (2.5 g), mp 155°–157° C.

EXAMPLE 16

α-Phenyl-2-(4-pyrimidine)ethanamine maleate

By following essentially the same procedure as described in Example 15 above and substituting 4-methylpyrimidine for 2-methylpyrazine the title compound was obtained as a white solid (1.6 g), mp 133°–136° C.

EXAMPLE 17

α-Phenyl-2-(3-pyridazine)ethanamine maleate

By following essentially the same procedure as described in Example 15 above and substituting 3-methylpyridazine for 2-methylpyrazine the title compound was obtained as a white solid (2.2 g), mp 142°–144° C.

EXAMPLE 18

α-Phenyl-2-[2-(3-methoxy)pyrazine]ethanamine mealeate

By following essentially the same procedure as described in Example 15 above and substituting 2-methoxy-3-methylpyrazine for 2-methylpyrazine the title compound was obtained as a white solid (1.4 g), mp 113°–116° C.

EXAMPLE 19

α-Phenyl-2-[2-(3-chloro)pyrazine]ethanamine hydrochloride

By following essentially the same procedure as described in Example 15 above and substituting 2-chloro-3-methylpyrazine for 2-methylpyrazine, the free base of the title compound was obtained as an oil. The base (2.7 g) was treated with an excess of isopropanol/HCl in isopropanol. The tan solid was collected by filtration and recrystallized from isopropanol/ethyl acetate to give the title compound as an off-white solid (1.7 g), mp 196°–198° C.

EXAMPLE 20

α-(2-furanyl)-2-pyridineethanamine dihydrochloride

By following essentially the same procedure as described in Example 4 above and substituting 2-furanaldehyde for 3-methyl-2-thiophene carboxaldehyde the free base of the title compound was obtained as an oil. The base (4.0 g) was treated with excess isopropanol/HCl in isopropanol. The off-white solid was collected by filtration and dried to give the title compound (4.5 g), mp 215°–220° C.

EXAMPLE 21

α-Phenyl-2-[2-(6-chloro)pyridine]ethanamine hydrochloride

By following essentially the same procedure as described in Example 4 above and substituting benzaldehyde and 6-chloro-2-picoline for 3-methyl-2-thiophene carboxaldehyde and 2-picoline respectively the free base of the title compound was obtained as an oil. The base (5.2 g) was treated with an excess of ethanol/HCl in ethanol. The white solid was collected by filtration and dried to give the title compound (1.3 g), mp 209°–212° C.

EXAMPLE 22

N-Ethyl-1-phenyl-2-(3-pyridazine)ethanamine hydrochloride

To a Parr bottle charged with platinum oxide (120 mg) was added a solution of α-phenyl-2-(3-pyridazine)ethanamine (as prepared in Example 17, 4.1 g, 0.02 mol) in 120 ml of ethanol followed by 1.73 ml (0.031 mol) of acetaldehyde under nitrogen. The mixture was subjected to hydrogenation at 2.7 atm (40 psi) of hydrogen for 15 minutes, filtered through celite, and the filtrate concentrated to give a dark oil (5.2 g). The oil was purified by chromatography on silica gel eluting with ammoniated $CH_3OH/CHCl_3$ [1:19–1:9] gradient, dissolved in absolute ethanol (20 ml), and made acidic by adding ethanol/HCl. The resulting off-white solid was collected by filtration and dried to give the title compound (1.1 g), mp 163°–164° C.

EXAMPLE 23

N-Ethyl-1-phenyl-2-(4-pyrimidine)ethanamine hydrochloride

By following essentially the same procedure as described in Example 22 above and substituting α-phenyl-2-(4-pyrimidine)ethanamine for α-phenyl-2-(3-pyridazine)ethanamine (as prepared in Example 16), the title compound was obtained as a white solid (1.4 g), mp 161°–162° C.

EXAMPLE 24

N-Ethyl-1-phenyl-2-(2-pyrazine)ethanamine hydrochloride

By following essentially the same procedure as described in Example 22 above and substituting α-phenyl-2-(2-pyrazine)ethanamine (as prepared in Example 15) for α-phenyl-2-(3-pyridazine)ethanamine, the title compound was obtained as a white solid (1.2 g), mp 205°–206° C.

EXAMPLE 25

N-Isopropyl-1-phenyl-2-(2-pyrazine)ethanamine fumarate

By following essentially the same procedure as described in Example 22 above and substituting α-phenyl-2-(2-pyrazine)ethanamine (as prepared in Example 15) and acetone for α-phenyl-2-(3-pyridazine)ethanamine and acetaldehyde respectively, and treating the purified free base with fumaric acid (1.2 equivalents) in ethanol/ethyl acetate the title compound was obtained as a white solid (2.3 g), mp 169°–170° C.

EXAMPLE 26

N-Methyl-1-phenyl-2-(2-pyrazine)ethanamine dihydrochloride

To a stirred mixture of α-phenyl-2-(2-pyrazine)ethanamine (as prepared in Example 15, 3.9 g, 0.02 mol), and NaOH (1.0 g, 0.024 mol) in a solvent mixture of 2 ml of water and 8 ml of t-butanol was added dropwise a solution of t-butyloxycarbonyl anhydride (5.9 g, 0.027 mol) in 2 ml of water and 7 ml of t-butanol. The reaction mixture was stirred at room temperature for 15 minutes, during which time a white solid had precipitated. An additional 8 ml of t-butanol was added, the mixture cooled to 0° C. and 1N sulphuric acid was added until pH 1–2 was obtained. The mixture was extracted with chloroform (3×), the organics combined, washed with brine, and dried. The resulting crude off-white solid (6.4 g) was slurried with ether, collected by filtration and dried to give purified product as a white solid (5.0 g).

To an ice-cooled solution of the white solid (3. g, 0.01 mol) and iodomethane (1 ml, 0.016 mol) in 50 ml of THF was added in portions sodium hydride (0.64 g, 0.016 mol, 60% dispersion in oil). The resulting mixture was allowed to warm to room temperature, stirred for 2 days, and partitioned between water and chloroform. The aqueous layer was extracted with $CHCl_3$ (2×), the organics combined, washed with water, brine, and dried. The resulting dark oil (4.5 g) was purified by chromatography on silica gel eluting with ammoniated 0–3% $CH_3OH/CHCl_3$ to give purified product as a yellow oil (2.5 g).

To a solution of the oil (1.9 g, 6 mmol) in 20 ml of $CH_3OH$ was added 1.3 ml of concentrated aqueous HCl, and the resulting mixture heated at reflux temperature for 1 hour. The mixture was concentrated to dryness to give a dark oil (2.4 g) which on standing in a solvent mixture of ethanol and ethyl acetate gave a pale yellow solid (1.3 g). Recrystallization of the solid from hot ethanol gave the title compound as an off-white solid (1.0 g), mp 157°–159° C.

EXAMPLE 27

α-Phenyl-2-[2-(6-hydroxymethyl)pyridine]ethanamine hydrochloride a) α-Phenyl-2-[2-(6-methyl)pyridine N-oxide]ethanamine By following essentially the same procedure as described in Example 15 above and substituting 2,6-lutidine N-oxide (2.5 equivalents) for 2-methylpyrazine the subtitle compound was obtained as a syrup after chromatography on silica gel.

b) N-trifluoroacetyl-α-Phenyl-2-[2-(6-hydroxymethyl)pyridine]ethanamine

To an ice-cooled solution of the product of step (a) (5.3 g, 0.023 mol) in DMF (dimethylformamide, 50 ml) was added dropwise with stirring 40 ml of trifluoroacetic anhydride (0.28 mol). The resulting mixture was allowed to warm to room temperature and stir for 2 days. The residue obtained after concentrating to near dryness was partitioned between ether and water, the aqueous layer separated and extracted with ether (3×). The organic extracts were combined, dried, and the resulting crude dark oil was purified by chromatography on silica gel to give the subtitle compound as an oil (3.6 g).

c) α-Phenyl-2-[2-(6-hydroxymethyl)pyridine]ethanamine hydrochloride

To a solution of the product of step (b) (2.6 g) in 50 ml of methanol was added 30 ml of 25% sodium hydroxide solution. The resulting mixture was heated at reflux temperature for 2 hours, cooled, concentrated to a small volume, and partitioned between ethyl acetate and water. The aqueous layer was separated and extracted with ethyl acetate (3×), the organic layers combined and dried. The resulting crude product was purified by chromatography on silica gel, dissolved in a solvent mixture of isopropanol and ether and treated with fumaric acid (1.1 equivalents). The white solid was collected by filtration and freeze dried from water (125 ml) to give the title compound as a white solid (0.7 g), mp 60° C. (softens).

EXAMPLE 28

6-[(2-Amino-2-phenyl)ethyl]-2-picolinamide dihydrochloride a) α-Phenyl-2-(2-pyridine N-oxide)ethanamine By following essentially the same procedure as described in Example 15 above and substituting picoline N-oxide for 2-methylpyrazine, the subtitle compound was obtained as a syrup after chromatography on silica gel.

b) N-Trifluoroacetyl-α-phenyl-2-(2-pyridine N-oxide)ethanamine

To an ice-cooled mixture of the product of step (a) (87.8 g, 0.4 mol) and sodium carbonate (123 g) in a solvent mixture of ether (2l) and THF (1l) was added dropwise trifluoroacetic anhydride (114 ml, 0.8 mol). The resulting mixture was allowed to warm to room temperature and stirred overnight. The mixture was then partitioned between ethyl acetate and water, the aqueous layer extracted with ethyl acetate (3×), the organic layers combined, dried and concentrated to give crude subtitle compound as a brown semi-solid (80.9 g).

c) N-Trifluoroacetyl-α-phenyl-2-[2-(6cyano)pyridine]ethanamine

To the product of step (b) was added dropwise dimethylsulphate (24.7 ml, 0.26 mol) and the resulting slurry heated at 100° C. for 2 hours. The cooled reaction mixture was taken up in 2l of water and added gradually to sodium cyanide (38.1 g, 0.78 mol) in a stirred solvent mixture of water and ethyl acetate. The dark solution was stirred for 2 hours, the organic layer separated, dried and concentrated to give crude subtitle compound as a dark solid (76.8 g). Chromatography on silica gel followed by recrystallization from ethyl acetate/hexanes gave purified title compound as a tan solid (16.6 g).

d) 6-[(2-trifluoroacetamido-2-phenyl)ethyl]-2-picolinamide

A solution of the product of step (c) (3.82 g, 0.012 mol) in in 120 ml of acetone was added to a mixture of 120 ml of 15% hydrogen peroxide solution and 24 ml of 1N sodium hydroxide. The resulting mixture was heated at 55° C. for 2 hours, concentrated to near dryness and the residue partitioned between water and ethyl acetate. The organic layer was separated, dried and concentrated to give crude subtitle compound as a yellow solid (5.6 g). The solid was subjected to chromatography on silica gel to give the subtitle compound as an off-white solid (3.4 g).

e) 6-[(2-Amino-2-phenyl)ethyl]-2-picolinamide dihydrochloride

A mixture of the product of step (b), potassium carbonate (7 g), water (25 ml), and methanol (100 ml) was heated at reflux temperature for 2 hours. After cooling, the mixture was concentrated to near dryness and the residue triturated with $CH_3OH/CHCl_3$[1:5] to afford a crude solid product. Purification by chromatography on silica gel gave an off-white solid which was dissolved in ethanol/ether and made acidic by adding ethanol/HCl. The white solid was collected by filtration and freeze dried from water to give the title compound (1.25 g), mp 146°–149° C.

EXAMPLE 29

α-Phenyl-2-[2-(6-amino)pyridine]ethanamine dihydrochloride

To an ice-cooled stirred solution of KOH (1.1 g, 0.019 mol) in 90 ml of methanol was added in one portion of 6-[(2-trifluoroacetamido-2-phenyl)ethyl]-2-picolinamide [as prepared in Example 28(a), 3.27 g, 9.7 mmol]. When dissolution was complete iodobenzene diacetate (3.12 g, 0.019 mol) was added in one portion and the resulting mixture stirred at 0° C. for 30 minutes and then at room temperature for 1 hour. The volatiles were evaporated and the residue partitioned between water and chloroform. The organic layer was separated, dried and concentrated to give an off-white solid which was recrystallized from ethyl acetate/hexanes to give a white solid (2.95 g).

A solution of the white solid in 250 ml of concentrated aqueous hydrochloric acid was heated at reflux temperature for 20 hours, then concentrated to near dryness to give a yellow semi-solid residue. Recrystallization from ethanol/$H_2O$/ethyl acetate followed by freeze drying from water gave the title compound as an off-white solid (1.56 g), mp 265°–272° C.

EXAMPLE 30

α-Phenyl-2-[2-(6-amidino)pyridine]ethanamine dihydrochloride a) 6-cyano-2-(2-oxo-2-phenylethyl)-pyridine To a solution of 2-cyano-6-methylpyridine (9.7 g, 0.082 mol) in 400 ml of dry THF at −78° C. was added dropwise 90 ml of a 1M solution of lithium bis(trimethylsilyl)amide in THF. After stirring for 30 minutes a solution of methyl benzoate (30 ml, 0.245 mol) in 50 ml of THF was added dropwise. The resulting mixture was allowed to warm to room temperature and stirred overnight. The mixture was cooled to 0° C., quenched with 1N HCl, made basic with 15% NaOH solution, and extracted with ethyl acetate (3×). The organic layer was separated, dried, and concentrated to give crude material which was purified by chromatography on silica gel to give 2.5 g of the subtitle compound.

b) α-Phenyl-2-[2-(6-amidino)pyridine]ethanamine dihydrochloride

A mixture of the ketone obtained above, hydroxylamine hydrochloride (1.5 g), and sodium acetate (1.85 g) in 50 ml of 50% aqueous ethanol was heated at 50° C. for 12 hours. The mixture was evaporated to half volume, extracted with ethyl acetate (3×), and the organic extracts combined and dried. The resulting crude product was purified by chromatography on silica gel to give 2.4 g of white solid.

A solution of the white solid and 10% Pd-C catalyst (1 g) in 60 ml of glacial acetic acid was subjected to 2.7 atm (40psi) of hydrogen on a Parr apparatus for 2 days. The reaction mixture was filtered through celite, the filtrate concentrated to dryness and the resulting crude product purified by chromatography on silica gel to give an oil (2.7 g). The oil was dissolved in isopropanol, made acidic with isopropanol/HCl and the resulting solid recrystallized from ethanol/ether and freeze-dried from water to give the title compound as a white solid (1.7 g), mp 175°–185° C.

EXAMPLE 31

The title compound of Example 1 was tested for anticonvulsant activity against MES induced convulsions and found to have an $ED_{50}$ (po) of 10.4 mg/kg.

We claim:

1. A compound of the formula I,

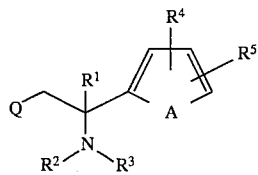

I wherein

A represents CH=CH;

Q represents pyrazine having substituents $R^6$ and $R^7$;

$R^1$ represents H or $C_{1-6}$ alkyl;

$R^2$ represents H, $C_{1-6}$ alkyl, $C_{3-6}$ alkenyl, $C_{3-6}$ alkynyl, $C_{3-6}$ cycloalkyl or $NH_2CH_2CO-$;

$R^3$ represents H, $C_{1-6}$ alkyl, $C_{3-6}$ alkenyl or $C_{3-6}$ alkynyl;

$R^4$ and $R^5$ independently represent H, OH, $C_{1-6}$ alkoxy, $C_{1-6}$ alkyl, halogen, trifluoromethyl or $NR^8R^9$;

$R^6$ and $R^7$ independently represent H, OH, $C_{1-6}$ alkoxy, $C_{1-6}$ alkyl, halogen, trifluoromethyl, $C_{1-6}$ hydroxyalkyl, amidino, $CONH_2$ or $NR^8R^9$;

in addition, $R^6$ and $R^7$ may independently represent O when substituted on N;

$R^8$ and $R^9$ independently represent H or $C_{1-6}$ alkyl;

and pharmaceutically acceptable salts thereof.

2. A compound as claimed in claim 1, wherein Q represents 2-pyrazinyl.

3. A compound as claimed in claim 1, wherein $R^1$ represents $C_{1-6}$ alkyl.

4. A compound as claimed in claim 1, wherein $R^4$, $R^5$, $R^6$ and $R^7$ each represent H.

5. A compound as claimed in claim 1, which is

α-Phenyl-2-(2-pyrazine)ethanamine,

α-Phenyl-2-[2-(3-methoxy)pyrazine]ethanamine,

α-Phenyl-2-[2-(3-chloro)pyrazine]ethanamine,

N-Ethyl-1-phenyl-2-(2-pyrazine)ethanamine,

N-Isopropyl-1-phenyl-2-(2-pyrazine)ethanamine,

N-Methyl-1-phenyl-2-(2-pyrazine)ethanamine, or a pharmaceutically acceptable salt thereof.

6. A pharmaceutical formulation comprising a compound of formula I, as defined in claim 1, or a pharmaceutically acceptable salt thereof, in association with a pharmaceutically acceptable adjuvant, diluent or carrier.

7. A method of treatment of neurological disorders selected from the group consisting of stroke and cerebral ischaemia, which comprises administering to a patient in need of such treatment a therapeutically effective amount of a compound of formula I, as defined in claim 1, or a pharmaceutically acceptable salt thereof.

* * * * *

UNITED STATES PATENT AND TRADEMARK OFFICE
CERTIFICATE OF CORRECTION

PATENT NO. : 5,607,935
DATED : March 4, 1997
INVENTOR(S) : GRIFFITH et al

It is certified that error appears in the above-identified patent and that said letters patent is hereby corrected as shown below:

```
On the title page: Item [75]
```
delete "Robert J. Griffith" and replace by --Robert J. Murray--.

Signed and Sealed this

Nineteenth Day of August, 1997

Attest:

BRUCE LEHMAN

Attesting Officer

Commissioner of Patents and Trademarks